(12) United States Patent
Forsland et al.

(10) Patent No.: US 10,990,175 B2
(45) Date of Patent: Apr. 27, 2021

(54) BRAIN COMPUTER INTERFACE FOR AUGMENTED REALITY

(71) Applicant: Cognixion, Santa Barbara, CA (US)

(72) Inventors: Andreas Forsland, Santa Barbara, CA (US); Leonard Zerman, Santa Barbara, CA (US)

(73) Assignee: Cognixion, Santa Barbara, CA (US)

(*) Notice: Subject to any disclaimer, the term of this patent is extended or adjusted under 35 U.S.C. 154(b) by 25 days.

(21) Appl. No.: 15/929,085

(22) Filed: Jan. 9, 2019

(65) Prior Publication Data

US 2020/0133393 A1    Apr. 30, 2020

Related U.S. Application Data

(60) Provisional application No. 62/752,133, filed on Oct. 29, 2018.

(51) Int. Cl.

| | |
|---|---|
| *G06F 3/01* | (2006.01) |
| *G06T 19/00* | (2011.01) |
| *G02B 27/01* | (2006.01) |
| *A61B 5/38* | (2021.01) |
| *A61B 5/316* | (2021.01) |
| *A61B 5/378* | (2021.01) |

(52) U.S. Cl.
CPC .............. *G06F 3/015* (2013.01); *A61B 5/316* (2021.01); *A61B 5/378* (2021.01); *A61B 5/38* (2021.01); *G02B 27/017* (2013.01); *G06T 19/006* (2013.01)

(58) Field of Classification Search
None
See application file for complete search history.

(56) References Cited

U.S. PATENT DOCUMENTS

| | | | | |
|---|---|---|---|---|
| 2007/0284448 | A1* | 12/2007 | Wang | G06K 7/10722 235/462.45 |
| 2016/0077547 | A1* | 3/2016 | Aimone | G06F 3/012 345/8 |
| 2018/0217382 | A1* | 8/2018 | Urbach | G09G 3/001 |
| 2018/0239430 | A1* | 8/2018 | Tadi | F21V 5/007 |

* cited by examiner

*Primary Examiner* — Nicholas J Lee
(74) *Attorney, Agent, or Firm* — Rowan TELS LLC (57) ABSTRACT

A method and system of a brain computer interface in a headset including an augmented reality display, one or more sensors, a processing module, at least one biofeedback device, and a battery. The interface may include a printed circuit board that has the sensors to read bio-signals, provides biofeedback, and performs the processing, analyzing, and mapping of bio-signals into output. The output provides feedback via stimulation of multiple sensory brain systems of a user, including audio and visual on the augmented reality display, or audio and haptic in terms of vibration patterns that a human user may feel. All together this forms a closed-loop system, by detecting the bio-signal, then providing sensory-feedback, which in turn enhances the bio-signal.

11 Claims, 12 Drawing Sheets

BRAIN COMPUTER INTERFACE FOR AUGMENTED REALITY

CROSS REFERENCE TO RELATED APPLICATIONS

This application claims the benefit of U.S. provisional patent application Ser. No. 62/752,133, filed on Oct. 29, 2018, the contents of which are incorporated herein by reference in their entirety.

BACKGROUND

When typical brain-computer interfaces (BCIs) are used, an external device or a computer and monitor are required to process and act upon the brain signals from the BCI. This typically but not always requires a wired connection between BCI, and a variety of separate systems and devices for processing data, as well as displaying and synchronizing visual information with the BCI. Usually, the devices used for the brain-computer interface may require multiple dangling wires, which present multiple points of failure in the sense that if any of those wires are damaged, the brain-computer interface may fail to function. Typically, setting up a BCI system is time intensive and mostly location dependent in a room or lab. Additionally, there is a delay in receiving feedback based on the bio-signal from the brain, and another human may be required to be present in order to read the results from a separate device.

In addition to these problems, the typical printed circuit board used in BCIs is often flat in shape and may fail to offer practical functioning in field conditions. Therefore, there is a need for a brain-computer interface with an improved form factor and adequate internal field computing resources.

BRIEF SUMMARY

Disclosed herein are embodiments of a brain-computer interface and headset, which includes an augmented reality display, one or more sensors, a processing module, at least one biofeedback device, and a battery.

In some embodiments, the interface may include a printed circuit board that contoured in a shape that conforms to a human head. The board may be a flexible board or may be a board with separate sections linked together. In an embodiment, the board comprises three parts: a first area, a second area and a third area. The first area of the printed circuit board may comprise the analog front end and may input brain-to-surface (of the skin) bio-signals using strategically located sensors. The second area of the printed circuit board may perform the processing, analyzing and mapping of bio-signals into an output, including haptic, audio, and visual outputs to the augmented reality glasses. The third area of the printed circuit board may provide haptic and audio feedback. After experiencing feedback from all, or any of these three sensory modalities—audio, visual and haptic, a user may generate new and different bio-signals from the brain, and as such a feedback loop may result in creating and strengthening neural pathways that lead to successful behaviors and actions by the user of the headset.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

The present disclosure addresses problems of comfort, wireless mobility, usability, reliability and other constraints found in conventional BCI systems utilizing a novel contoured shape and consolidated on-board processing of bio-signal data utilizing a specially-designed printed circuit board within the headset. This ability to internally process bio-signals may reduce or eliminate the need for an external mobile device or computer to do the bio-signals processing.

The bio-signal data is collected from the sensors on or connected to the headset, input into the printed circuit board on the headset, processed on the headset, and then output to transducers including but not limited to visual, auditory, and haptic transducers. In an embodiment, the circuit board may have a variety of sensors connected to the analog front end. For example, the mounted EEG electrodes may be utilized, but there may also be EMG sensors attached to an arm or other body part wired to the circuit board for processing data from multiple sources, not just EEG on the head.

The output may for example be applied to an augmented reality headset that a user may wear. The senses that may be stimulated as biofeedback may include, e.g. output commands sent to inflatable bags for pressure, temperature for increasing therapeutic sensation, electrical stimulation, or even a command to an external device or system such as a prosthetic hand/arm/leg or wheelchair for controlled movement.

In response to these outputs, new and altered neural signals of the user's brain may be reinforced, thus establishing a feedback loop that may result in discovering unique and creative ways to translate intentions into new experiences by the user of the headset.

The headset may function standalone without reliance on an external mobile device or computer, making it portable and self-sufficient as a "read-only" device, i.e., no ability to display augmented reality. Alternatively, it may communicate wirelessly with a mobile device or computer, providing output based on the bio-signals from the user of the headset. The headset is a unique design that consolidates more processing power into a smaller package than conventional BCI headsets. The portability factor may make a significant impact on individuals who want to have this experience in locations that are away from modern conveniences, as well as for people who are disabled. For example, one of the uses of this device may include an augmented assisted communications device or a remote control device. The systems and devices described in this disclosure may assist people who otherwise have a hard time communicating or enough physical ability to control their environment well. The brain signals of such people may be able to communicate their thoughts or remotely control objects in their environment, as opposed to verbal or hand-based communications.

One embodiment comprises a fully self-contained EEG (electroencephalography) headset device that is specifically designed for the sensing and reporting of Visual Evoked Potential (VEP) matches, and optionally interfacing to a host computing device as a human Interface Device (HID) over Generic Attributes (GATT) device keyboards or mouse interfaces. In an embodiment, the Visual Evocation may be a steady state Visual Evoked Potential (SSVEP).

The self-contained device may comprise a headband or other external scalp sensor contact arrangement with one or more sensors. The device may also include support circuitry, such as a sensor amplifier, CPU, Analog to Digital (A2D) converter, and BLE (Bluetooth Low Energy) that interfaces with the HID over GATT protocol to a host. Acting as a HID wireless keyboard or mouse interface, this self-contained device may be used to control any HID interface compatible devices including but not limited to desktop computer, mobile devices and home appliances and media and entertainment equipment.

The device may be configurable for: (a) VEP matches on different frequencies that the device may monitor; (b) power threshold for the frequency; and (c) the number of consecutive repeated cycles over the threshold. The device may generate a configurable associated HID keyboard or mouse report to the HID Host. This capability may allow for direct control over iOS, Android, OSX, Windows, and Linux devices.

Artificial Intelligence (AI) Section:

The BCI may utilize AI for pattern-recognition and personalization. Traditional BCI+AI solutions are limited to fixed locations, expensive equipment, and ultra-high-speed continuous Internet connections.

The BCI may utilize an "Offline-First" design approach. The Offline-First techniques optimize and personalize the BCI performance even when offline.

When online, Machine Learning (ML) training is applied to create an individualized Recognizer-Categorizer (RC). Derived outputs of the ML training are stored into an Expert system (ES) knowledgebase in the cloud.

The ML & ES are not used in a conventional real-time system. The Synthesized Insights (SIs) derived from the ML & ES are used in a novel way to generate individualized executable Recognizer-Categorizers that may be automatically loaded into the BCI device (e.g., storage of the printed circuit board) for offline usage.

The present disclosure is directed to methods including AI utilized in the cloud to enhance resource constrained IoT. The apparatus in the disclosure include wearable and implantable devices that run individualized code locally generated by AI where a continuous, ultra-broadband streaming connection to the cloud is not reliable.

This disclosure provides solutions to adding AI to mobile device that cannot support AI locally or in a mobile context. In addition to processing brainwave data utilizing AI, the methods and systems developed for this BCI+AI may also be generally applicable to a wide-range of resource-constrained IoT, wearable and implantable devices.

In embodiments of a BCI headset, several AI techniques may be utilized. ML may be utilized as an auto-tuning dynamic noise reducer, a feature extractor, and a Recognizer-Categorizer. It is also a pipeline of training data input into the ES knowledgebase. The ES evaluates recognized brainwave patterns that are leveraged into the offline RCs. The ES has the necessary knowledge to create personalized and AI optimized RCs that may operate locally on Resource Constrained Devices (RCDs). An RCD may be a device that has limited processing and storage capabilities, and that often runs on batteries. This may offer a superior robustness and functionality for BCI that conventional techniques would not. Offline ML training feedback is incorporated by storing EEG EPOCs of successful recognition matches for re-integration into training sets synchronized upon the next online session.

The BCI headset may be a battery-powered, wireless, consumer-grade bio-signal sensing device comprising a two-sensor, three-contact point (2 sensors, ground-reference), a processor, and BLE (Bluetooth Low Energy) connectivity, specifically designed for the detection and processing of SSVEP brain signals to act as a BCI by only monitoring cranial points ($O_1$-$O_2$).

The present disclosure is directed to a brain computer interface in a headset that may correlate the printed circuit board (PCB) with brain waves and other bio-signal sources that are being processed. The PCB may utilize a microcontroller that includes a Bluetooth low energy module, a microprocessor, and a USB bridge. Further, in an embodiment, the EEG Analog-to-Digital processor includes an analog front end that receives channels using Texas Instruments ADS1299, which sends out signals through a serial peripheral interface (SPI) buffer to a microprocessor. The brain waves may be recorded using a micro SD. Additionally, the user may download music, sounds, or any haptic sequences, into the micro SD. In an embodiment, the headset may include a motor amplifier OLED module, which may be a 2 line by 180-pixel OLED such as an I2C OLED. From a visual perspective, the OLED module provides a feedback mechanism that may allow the user to view and or modify onboard BCI settings.

The haptic Motor Controller may include a built-in microcontroller chip that includes fundamental haptic vibrations. The user may stack those vibrations and may also create vibrations based on audio, or setup the haptic vibrations to make the headset vibrate to the music.

Audio feedback may include various fundamental tones. In an embodiment, the user may Add, Modify, or Manage audio feedback on the brain computer interface.

Operating Modes

Four modes of operation of the BCI headset may include: Raw, Simmer, Cooked, and human interface device-keyboard (HID-KB).

Raw Mode:

The raw mode may stream the full bio-signal sensor data stream, which may include an EEG sensor stream, for further processing locally or in the cloud via a mobile or desktop internet connected device which may filter, recognize, or interact with the data. This mode is useful for training an AI and/or cloud-based recognition system.

Simmer Mode:

The simmer mode is a hybrid combination between the Raw and Cooked modes. The on-board processor may intersperse the raw data stream with custom (Cooked) messages. This mode is most useful when training an AI and/or cloud-based recognition system and comparing it to the local recognizer and diagnoses.

Cooked Mode:

The cooked mode is a fully processed custom message that may be generated by the local recognizer and diagnoses. No Raw data is passed. This reduces the bandwidth required for operation.

HID-KB Mode:

The HID-KB mode configures the headset interface to appear to be a standard Bluetooth keyboard. This allows the headset to work with many applications including but not limited to desktop computer, mobile devices and home appliances and media and entertainment equipment. One advantage of HID-KB mode is to allow SSVEP to be used with the operating system accessibility features. It also may allow the headset the universal access to be utilized with many computers and operating systems that can utilize a Bluetooth keyboard. In an embodiment, the printed circuit board can emulate a Bluetooth keyboard and output to a mobile device, a computer, a car windshield, a plane windshield, a motorcycle visor, a motorcycle helmet, virtual reality glasses, mixed reality glasses, or the augmented reality glasses at least one of: a letter; a character; a number; and combinations thereof.

Device Construction

The two main sensors may be moved to the center or front of the user's head, the headset may efficiently detect and track various brain waves, such as beta waves or theta waves. The headset's implementation is not limited to two sensors but has the ability to have up to eight sensors, a ground, and a reference.

The headset and printed circuit board are sensitive to visually evoked potentials, audio evoked potentials, and motion evoked potentials. They are also sensitive to steady state visually evoked potentials in the AR headset, which includes a blinking light.

In one embodiment of the printed circuit board, the printed circuit board is limited in functionality to only visually evoked potentials, which allows for even faster processing entirely on the printed circuit board, and without the use of the cloud or an external computer.

In another embodiment of the printed circuit board, the printed circuit board is limited in functionality to only audio evoked potentials, which allows for even faster processing entirely on the printed circuit board, and without the use of the cloud or an external computer.

In another embodiment of the printed circuit board, the printed circuit board is limited in functionality to only haptic evoked potentials, which allows for even faster processing entirely on the printed circuit board, and without the use of the cloud or an external computer.

The printed circuit board may be preconfigured to map certain inputs from EEG (Electroencephalography), ECG (Electrocardiography), EMG (Electromyography), EOG (ElectroOculography), functional near-infrared spectroscopy (fNIRS), ECG, EEG, or other bio-signals, to particular types of feedback. The printed circuit board is configurable in terms of sound, music, words, visuals that are projected, and haptic files. The printed circuit board also has defaults of sound files, haptic files, certain algorithms for feature extraction, and pattern matching.

For example, the headset can be preconfigured to output the letter "A" when the printed circuit board reads the signal 10 hertz. Similarly, all alphabet, numbers, words, music and haptic vibrations may be mapped to an audio, visual or haptic input.

Furthermore, such pre-configurations can be customized to each user, such that there may exist customized vibration files, sound files, or different algorithms that are specific to a customer or user. These pre-configurations may be implemented wirelessly from an application, so the user does not have to plug into the USB of the printed circuit board.

For example, for given 3 frequencies, 7, 11, and 19 hertz, accessibility controls may be set to move to previous item, next item, or select item respectively. For example, if the printed circuit board reads the signal 7 hertz, then the "previous item" control may pop up on the AR headset.

In an embodiment, each user may have a dedicated 'private cloud' with all of their own data, personalized files and preferences, allowing the BCI to synchronize with the server when it connects to the internet.

In an embodiment, Over the Air downloads or firmware updates may be pushed to the BCI. The updates may be event-based changes or full system updates.

The connection used to attach the printed circuit board to the augmented reality glasses may be severed, thus enabling the printed circuit board to be connected to another pair of augmented reality glasses while maintaining all the functionality of the printed circuit board. The headset is capable of functioning with different augmented reality glasses, such as Microsoft Hololens™, Magic Leap™, and other products that can provide augmented reality through a visual display for a human being.

In an embodiment, a system of a brain computer interface in a headset includes: an augmented reality display; one or more sensors for reading a bio-signal from a user; a processing module, including a processor that analyzes and maps the bio-signal into an output on the augmented reality display; at least one biofeedback device in communication with the processing module, wherein the at least one biofeedback device provides feedback to the user; and a battery, wherein the battery provides power to at least one of the augmented reality display, the one or more sensors, the processing module, the at least one biofeedback device, and combinations thereof.

In an embodiment, a method of implementing a brain computer interface (BCI) in a headset includes utilizing an augmented reality display; utilizing one or more sensors for reading a bio-signal from a user; utilizing a processing module, including a processor that analyzes and maps the bio-signal into an output on the augmented reality display; utilizing at least one biofeedback device in communication with the processing module, wherein the at least one biofeedback device provides feedback to the user; and utilizing a battery, wherein the battery provides power to at least one of the augmented reality display, the one or more sensors, the processing module, the at least one biofeedback device, and combinations thereof.

The headset addresses the difficult commercial problem of resource constraints in BCI headsets, while improving functionality over conventional designs. The headset may also liberate users with full mobility, which makes it possible for researchers to perform true longitudinal studies in the field, as well as end users greater freedom to explore and interact with their environment.

The bio-signals are processed and analyzed in real-time. By doing more processing on the printed circuit board, costs are reduced by eliminating additional electronic equipment and reducing the amount of costly time and effort to setup and use it, thereby enabling more frequent use.

Furthermore, the latency of feedback responses is reduced through the augmented reality, haptic, and/or audio systems.

Figure 1:
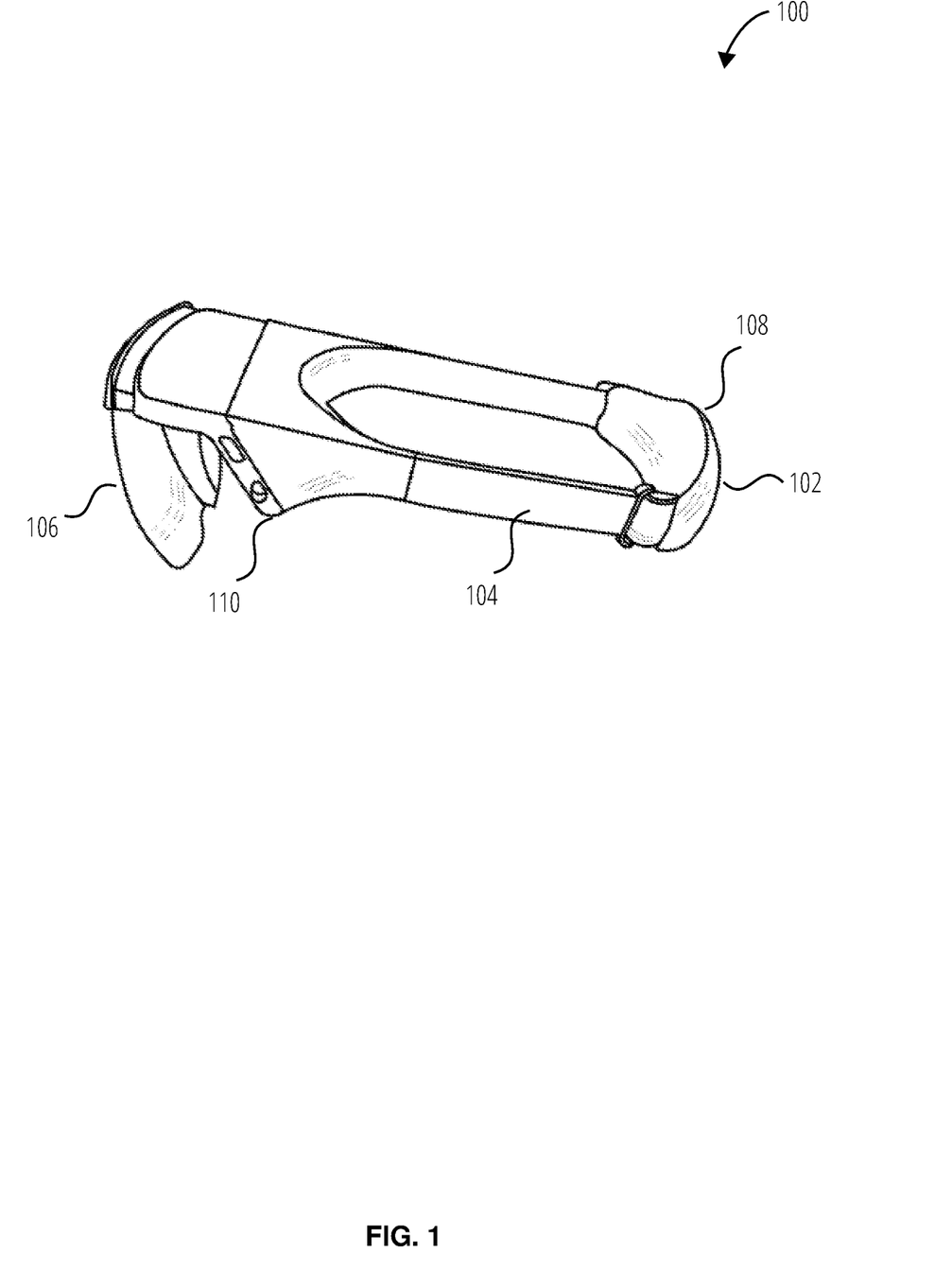
FIG. 1 illustrates a headset 100 in accordance with one embodiment.

Referring now to the drawings, FIG. 1 illustrates an embodiment of a headset 100 that comprises a PCB 102, a strap 104, a display 106, a contoured sleeve 108, and a visual display source 110. The display 106 and visual display source 110 may be any AR headset, and is not limited thereto. The PCB 102 is curved in shape to contour around the back of a human head. The contoured sleeve 108 secures the PCB 102 and other items such as batteries. The strap 104 may circumvent the PCB 102 and around the back of the human head and maintain the headset 100 in contact with the back of the human head. In some embodiments, the strap 104 traverses the contoured sleeve 108; however, the strap 104 may also traverse the outside rear surface of the contoured sleeve 108 or may be manufactured as a part of the contoured sleeve 108. The strap 104 may couple the PCB 102 electrically and physically to the display 106 and the visual display source 110. The PCB 102 may output a video signal to a user through the visual display source 110 and display 106. In some embodiments, the display 106 provides augmented reality images. The headset 100 is an exemplary example of a headset useful for the systems and methods of this disclosure, and is not limited to the components shown in FIG. 1 or FIG. 2.

Figure 2:
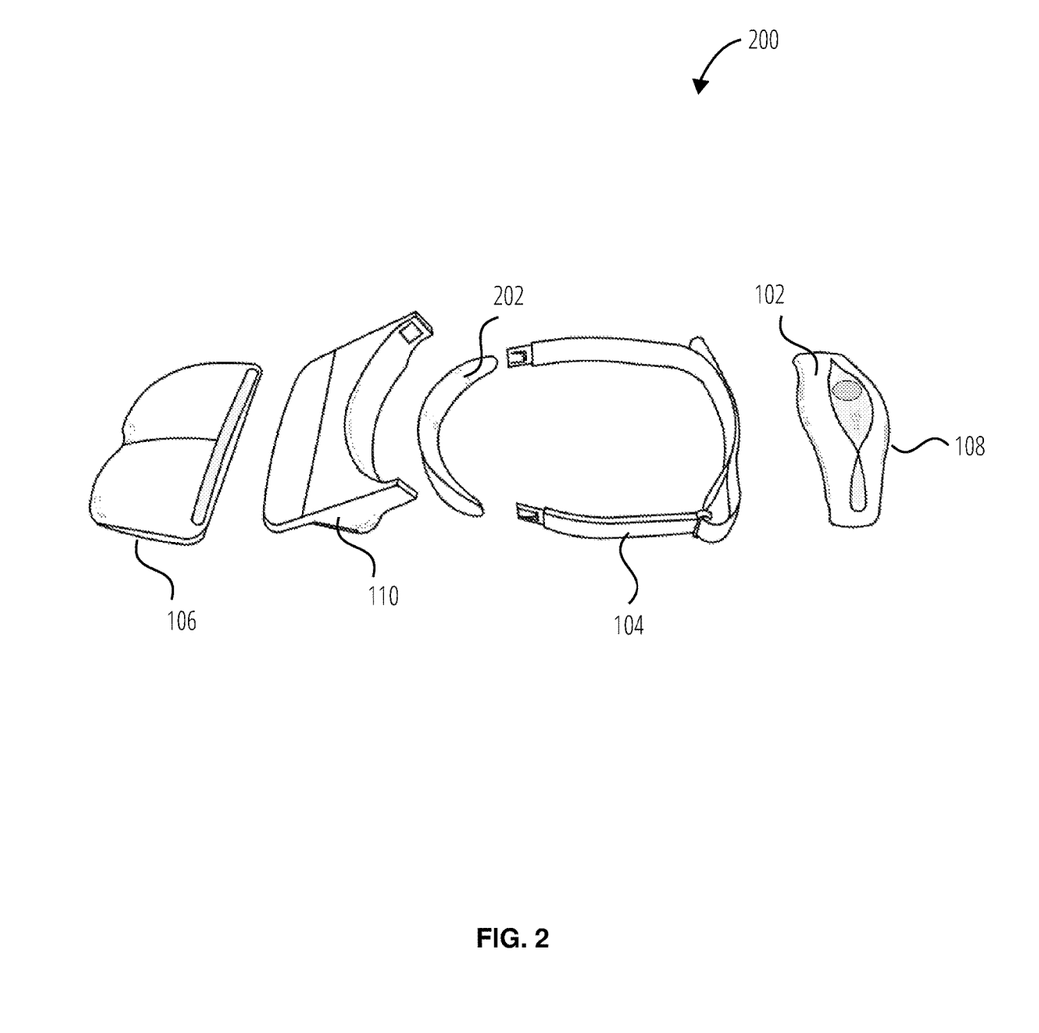
FIG. 2 illustrates a disassembled BCI headset 200 in accordance with one embodiment.

In FIG. 2, the disassembled BCI headset 200 comprises a PCB 102, a strap 104, a display 106, a contoured sleeve 108, a visual display source 110, and a pad 202. The pad 202 may be located on the visual display source 110 and provides a cushion between a user's forehead and the portion of the visual display source 110 in contact with the user's forehead. The disassembled BCI headset 200 is an exemplary example of a headset useful for the systems and methods of this disclosure, and is not limited to the components shown in FIG. 2.

Figure 3:
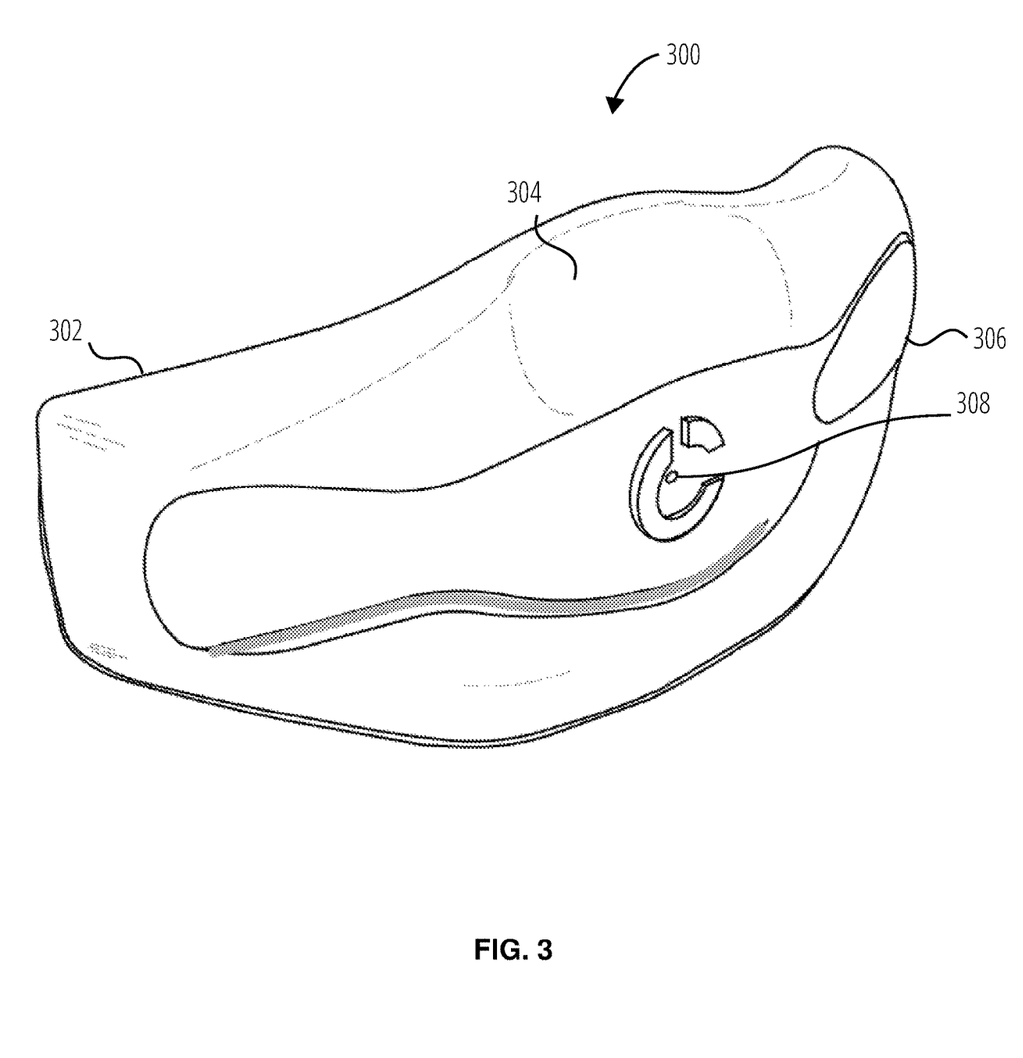
FIG. 3 illustrates a headset 300 in accordance with one embodiment.

FIG. 3 shows a front oblique view of headset 300 comprising a contoured sleeve 302, a cover 306, a led 308, and a PCB 304. The contoured sleeve 302 may include a PCB 304. The first area of the PCB 304 may include an analog front end and allows the headset 300 to read EEG (Electroencephalography), ECG (Electrocardiography), EMG (Electromyography), or other bio-signals. The cover 306 provides access to the PCB through the contoured sleeve 302.

In an embodiment, there is a hole (led 308) in the contoured sleeve 302 that allows a multicolor LED light to be piped out and visible externally to provide a user with color coded status indications such as power on/off, flickering, if there is data/activity, color coded for different modes, etc. The led 308 may be in the center of the contoured sleeve 302 but is not limited thereto. In an embodiment, this functional lighting indicator may be a single led light, multiple led lights, animated lights, etc. The light indicator functionality may be personalized for the individual user.

Figure 4:
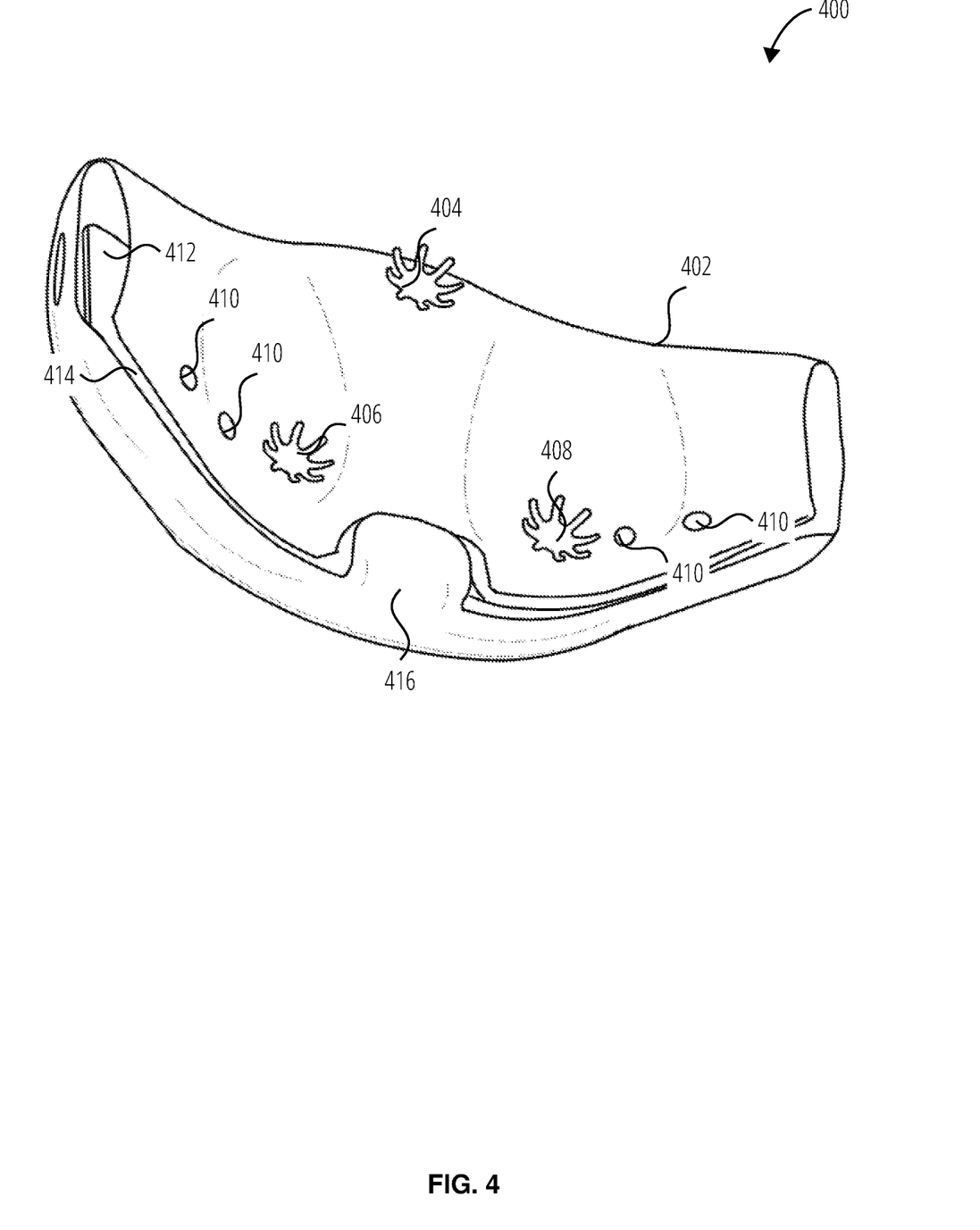
FIG. 4 illustrates a headset 400 in accordance with one embodiment.

Referring to FIG. 4, a portion of a headset 400 comprises a contoured sleeve 402, a sensor 404, a sensor 406, a sensor 408, additional sensors 410, a PCB 412, a slit 414, and a clasp 416. The contoured sleeve 402 may include 3 sunburst-type shapes on the portion of the headset that are formed to contact the human's head, the shapes representing sensor 404, sensor 406 and sensor 408. The shapes representing the sensors may be any shape. In an embodiment, the shape is recessed into the contoured sleeve 402. The recessed area enables the sensors to be more comfortable and stable. In some embodiments, the sensors may be adjusted up, down, left, or right. The sensor 404, sensor 406 and sensor 408 detect brain signals, and apply them to the PCB 412, where the PCB 412 processes brain signals. There are 4 additional sensors 410. These additional sensors may also sense brain signals and apply them to the PCB 412 for further processing.

In another embodiment of the headset 400, the headset only has 4 additional sensors 410, instead of 7 total sensors.

Different embodiments of the PCB 412 may utilize cables between break points in the printed circuit board, such that the layout of sensors can be 6 1×1 s or 3 2×1 s, or 3 1×2 s.

The contoured sleeve 402 may include a slit 414 between the rear surface and the bottom surface. The slit 414 may be opened by releasing the clasp 416 and spreading apart the bottom and rear of the contoured sleeve 402. This slit 414 may serve to allow exchangeability of different kinds of head straps.

Figure 5:
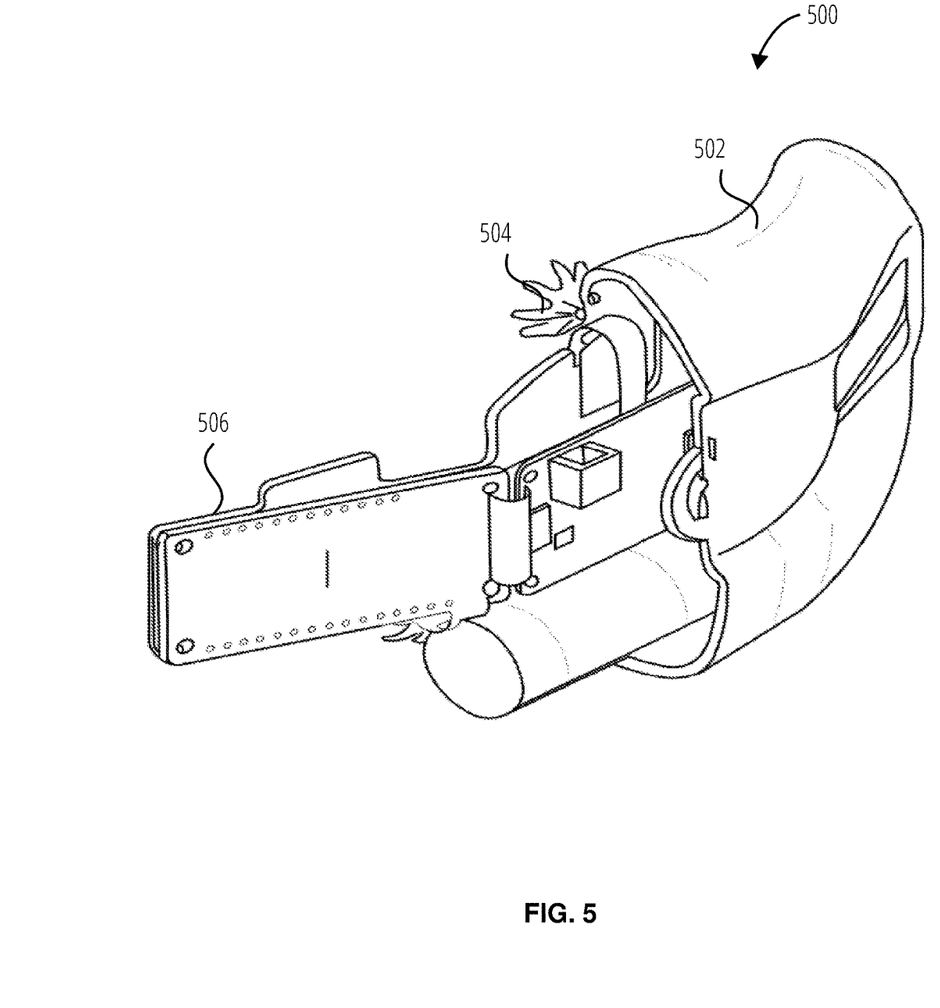
FIG. 5 illustrates a cross section of headset 500 in accordance with one embodiment.

Referring to FIG. 5, a cross section of headset 500 according to an embodiment includes a contoured sleeve 502, a third area 506 of the printed circuit board, and a sensor 504 attached to the contoured sleeve 502 of the headset. Although three areas are shown, the printed circuit board may be a single flexible board where the positioning of the components on the board is not critical.

The third area 506 provides haptic feedback. The bio-signals may be processed and analyzed in real-time. The bio-signals are processed locally in the headset 400 and therefore are not streamed online or in the cloud. This is referred to as localization.

Figure 6:
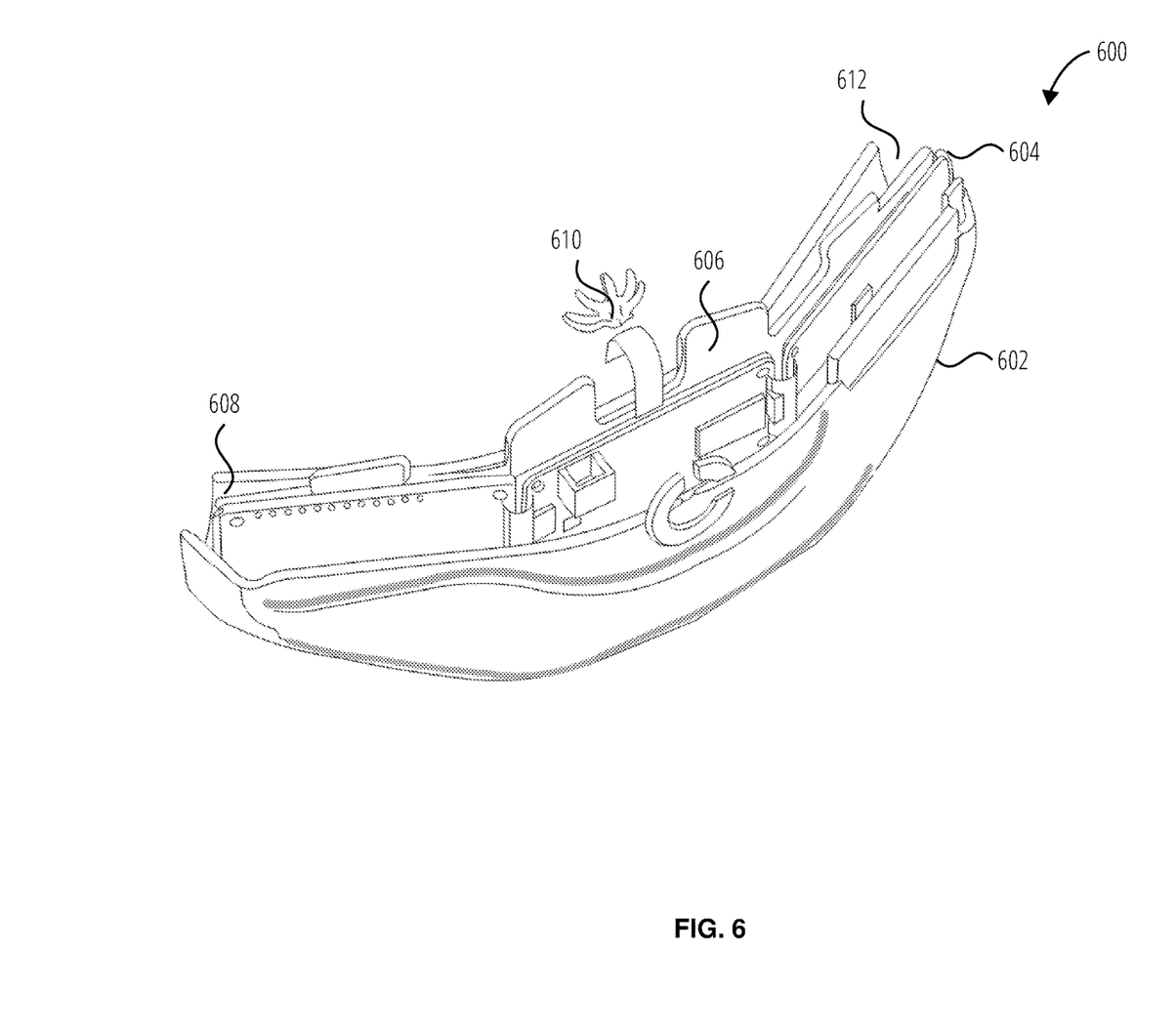
FIG. 6 illustrates a cross section of headset 600 in accordance with one embodiment.

Referring to FIG. 6, a cross section of headset 600 according to one embodiment includes a contoured sleeve 602, a first area 604, a second area 606, a third area 608, and a sensor 610. The top of the contoured sleeve 602 has been removed to show the embedded printed circuit board in the headset. A sensor 610 is attached to the third area 608 of the printed circuit board. The cross section of headset 600 also shows the first area 604 and the second area 606 of the printed circuit board. In an embodiment, there is a channel 612 area where an AR headset strap may pass through the inside of the BCI. The channel 612 may be present from one side of the BCI to the other (near the third area 608). In an embodiment, there is a hole on either side of the BCI where both ends of the AR headset strap may come through.

Figure 7:
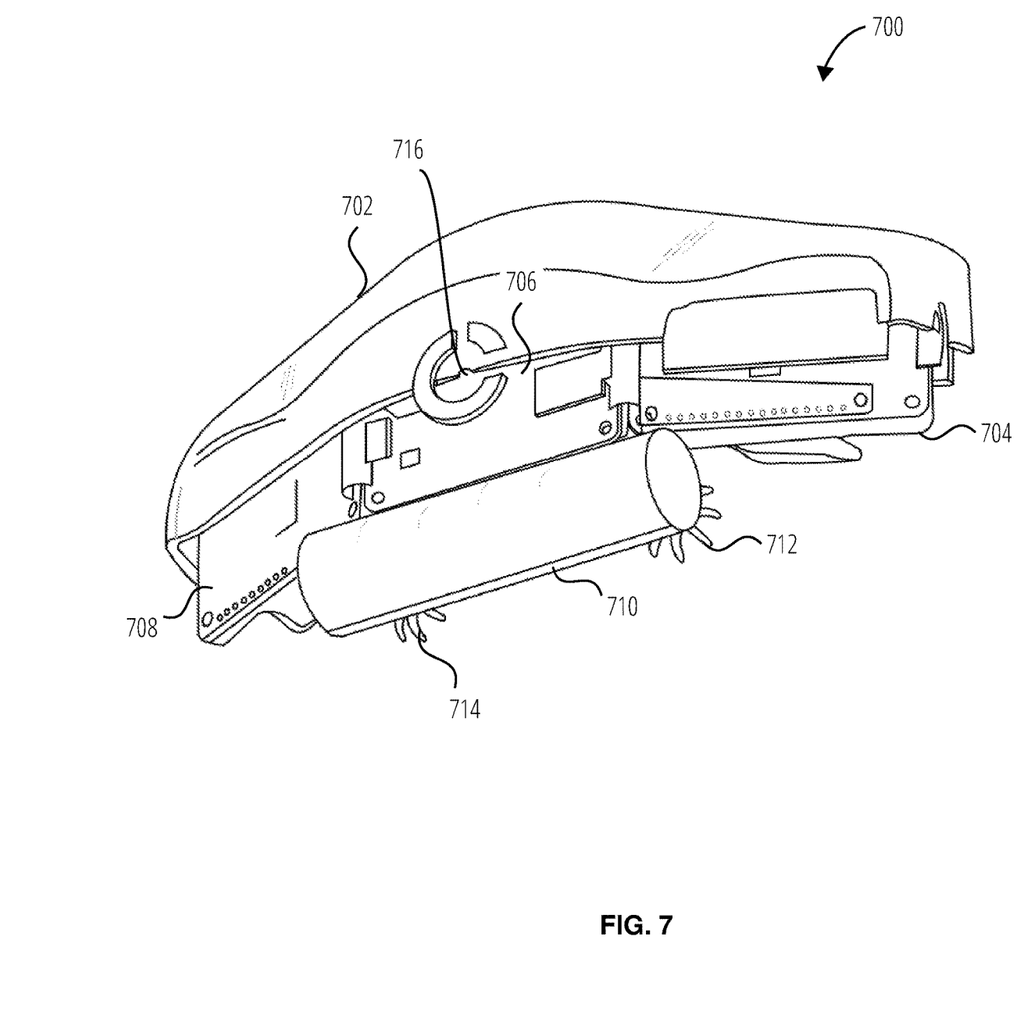
FIG. 7 illustrates a cross section view of headset 700 in accordance with one embodiment.

Referring to FIG. 7, a cross section view of headset 700 comprises a contoured sleeve 702, a first area 704, a second area 706, a third area 708, a battery 710, a sensor 712, and a sensor 714. The battery 710 may be a LiPo, LiOn, etc., battery and may be a custom shape/designed battery.

The cross-section view of headset 600 with the bottom of the case removed shows a PCB inside of contoured sleeve 702 and demonstrates how the PCB is embedded into the headset. The first area 704, the second area 706 and the third area 708 are shown on the PCB. A battery 710 is located in the bottom portion of the headset. There is a sensor 712 and a sensor 714 attached to the battery 710. The headset 600 may also have a status led 716.

Figure 8:
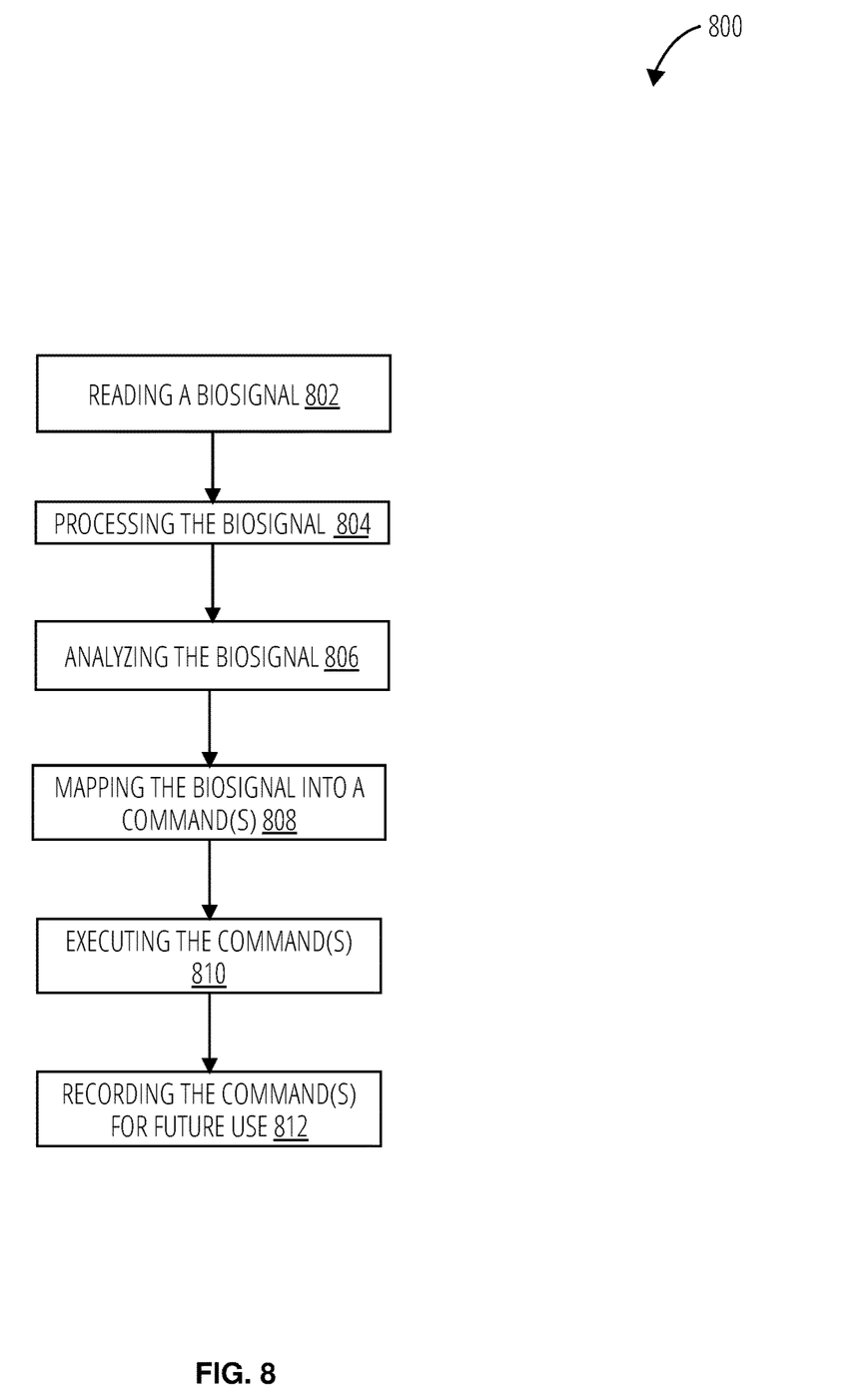
FIG. 8 illustrates a method 800 in accordance with one embodiment.

Referring to FIG. 8, a method 800 includes the steps involved to implement a brain computer interface in a headset. The steps include reading a bio-signal using the first area of the PCB as an analog front end (block 802), processing the captured bio-signal (block 804), analyzing the bio-signal (block 806), mapping the bio-signal into command(s) (block 808), executing the command(s) (block 810), and recording the command(s) for future use (block 812).

The method 800 may be a closed loop method for reading brainwaves via the BCI and writing to the brain via biofeedback through the user's somatosensory system (sight, sound, vibrations/haptics). In an embodiment, the closed loop system reads the visual cortex via the occipital lobe (visual) and writes to the somatosensory cortex (senses).

In an embodiment, the commend is at least one of the following: do nothing; log the data for later use; play an audio file; manipulate a visual element; play a vibration pattern; send a message or command to another device; remotely control a prosthetic limb; turn on/off the lights; change a tv channel, and combinations thereof.

In an embodiment, the commands may be recorded for future use and improved machine learning performance as well as human neural performance/recall as reinforcement learning.

In an embodiment, the bio-signal that the PCB can read includes at least one of EEG (Electroencephalography), ECG (Electrocardiography), EMG (Electromyography), EOG (Electroocculography), visually evoked potentials, steady state visually evoked potentials, steady state audio evoked potentials, and motion evoked potentials.

Figure 9:
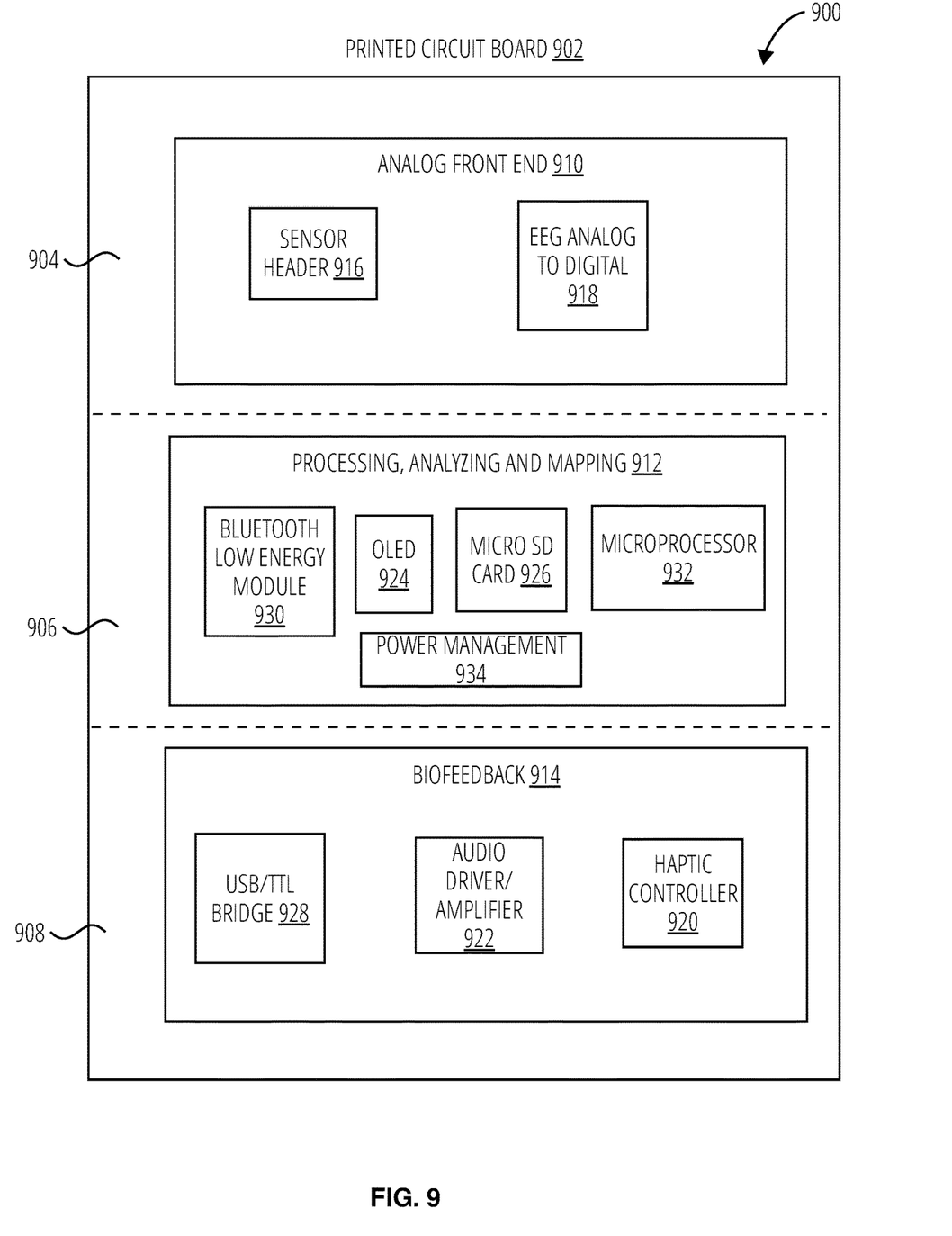
FIG. 9 illustrates a device 900 in accordance with one embodiment.

Referring to FIG. 9, a device 900 comprises a printed circuit board 902, a first area 904, a second area 906, a third area 908, an analog front end 910, processing, analyzing and mapping 912 logic, a biofeedback 914, a sensor header 916, an EEG analog to digital 918, a haptic controller 920, an audio driver/amplifier 922, an OLED 924, a micro sd card 926, a USB/TTL bridge 928, a Bluetooth low energy module 930, a microprocessor 932, and power management 834.

The printed circuit board 902 comprises three areas, the first area 904 (analog front end 910), the second area 906 (processing, analyzing and mapping 912) and the third area 908 (biofeedback 914).

The first area 904 is the analog front end 910 that includes sensor header 916, EEG analog to digital 918 converter and the like. The first area of the printed circuit board receives the bio-signal and converts it to a digital signal. The second area 906 includes Bluetooth low energy module 930, OLED 924, micro sd card 926, microprocessor 932, power management module 934, and the like. The second area of the printed circuit board processes and analyzes the bio-signal using the microprocessor 932 and maps the bio-signal into an output on the augmented reality glasses. The output may include audio and visual output or a haptic output. The power management module may control power to the various components and modules, including the Bluetooth low energy module 930. The third area 908 provides a biofeedback 914 using a USB/TTL bridge 928, an audio driver/amplifier 922, or a haptic controller 920.

Figure 10:
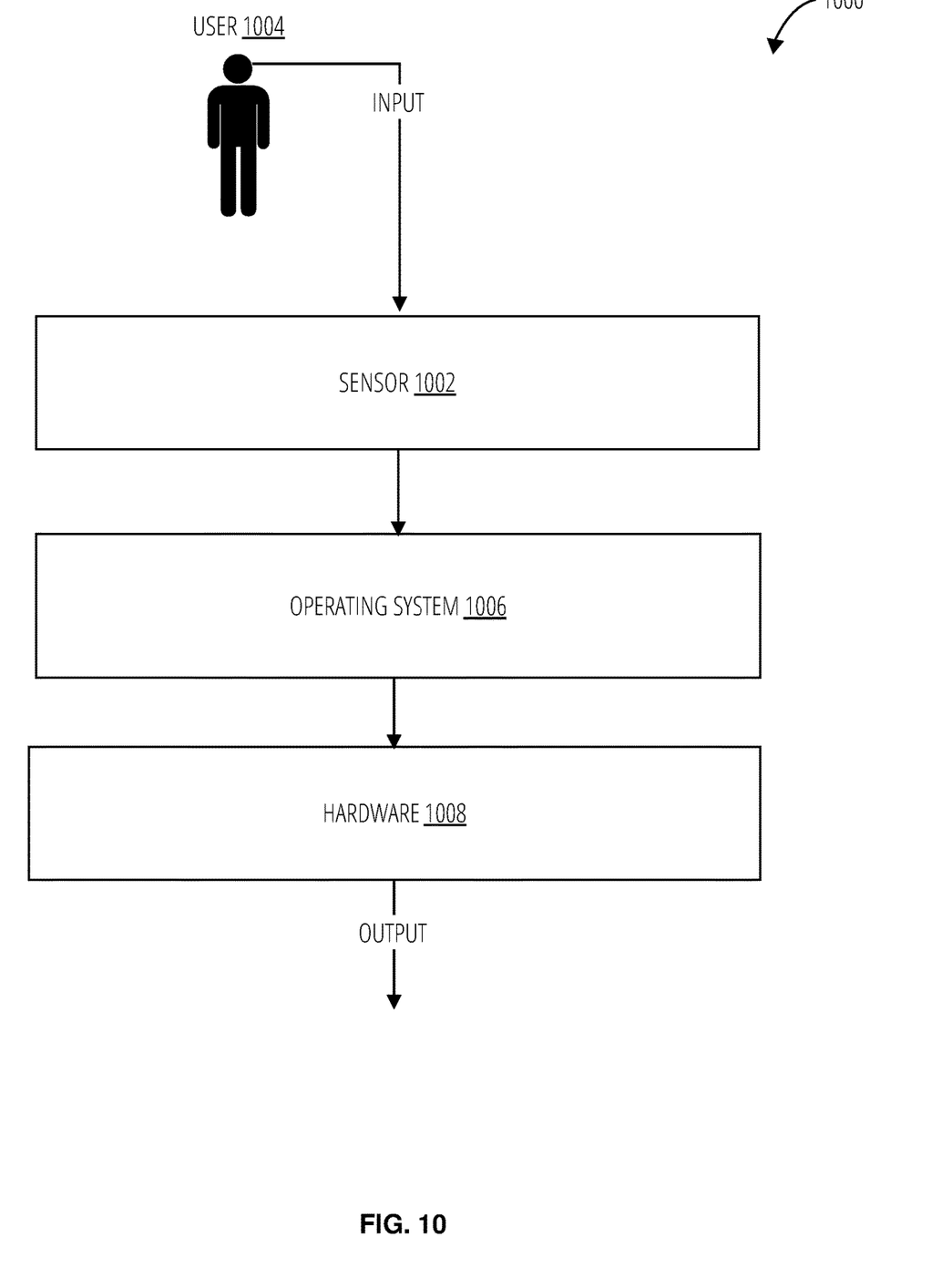
FIG. 10 illustrates a BCI+AR system 1000 in accordance with one embodiment.

FIG. 10 illustrates a BCI+AR system 1000 in accordance with one embodiment of the disclosure. A sensor 1002 receives signals from a user 1004. These signals trigger an event in the operating system 1006. The signals are then mapped to an output using the hardware 1008. The output may include audio and video or may be a haptic output including haptic vibration patterns.

Figure 11:
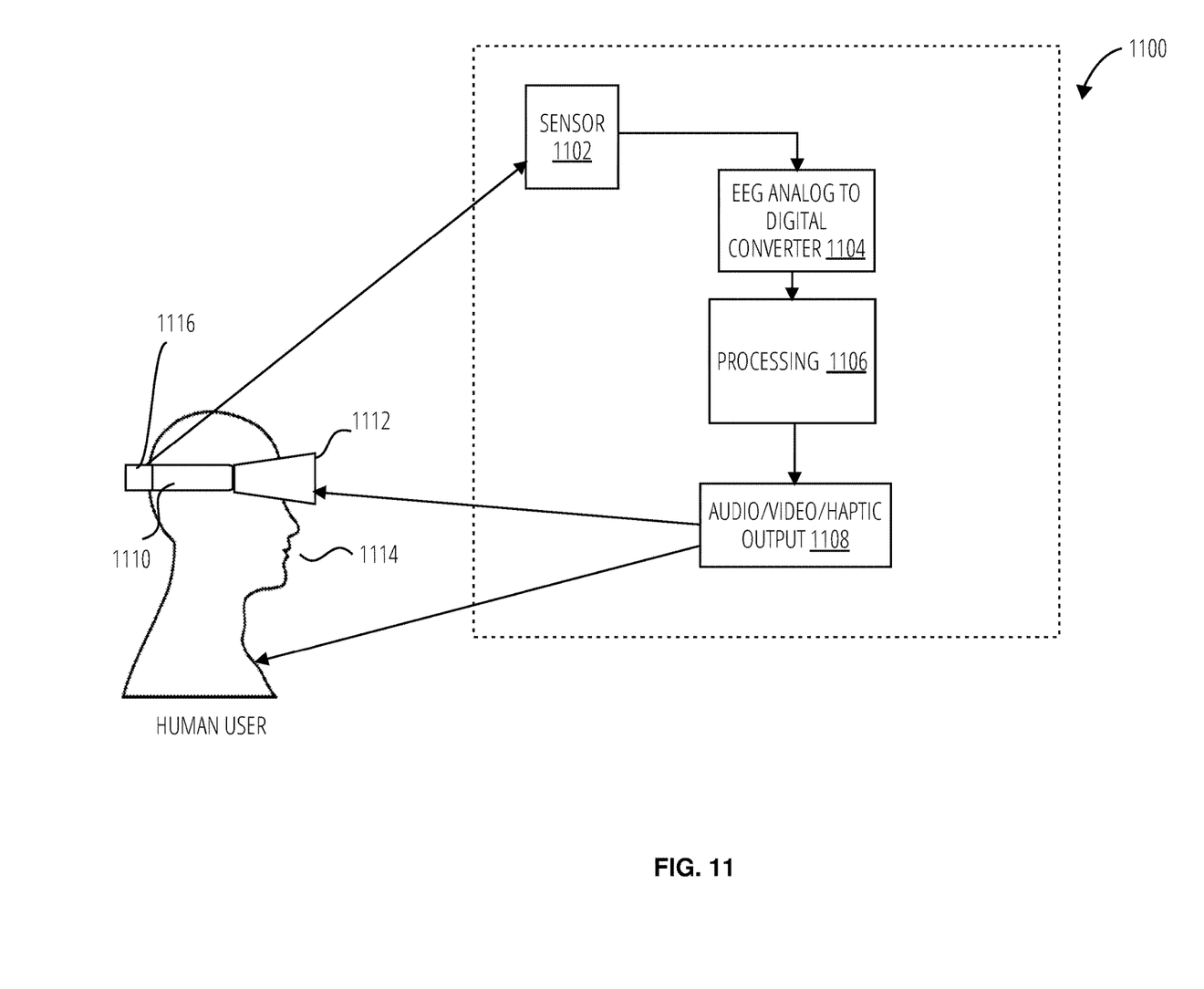
FIG. 11 illustrates a BCI+AR environment 1100 in accordance with one embodiment.

FIG. 11 illustrates an embodiment of a BCI+AR environment 1100. The BCI+AR environment 1100 comprises a sensor 1102, an EEG analog to digital converter 1104, an Audio/Video/Haptic Output 1108, a processing 1106, a strap 1110, an augmented reality glasses 1112, a human user 1114, and a BCI 1116. A human user 1114 is wearing BCI 1116, which is part of a headset. When the human user 1114 interacts with the environment, the sensor 1102, located within the BCI 1116, reads the intentions and triggers the operating system. The EEG analog to digital converter 1104 receives the sensor 1102 output (e.g., intention). EEG analog to digital converter 1104 transforms the sensor output into a digital signal which is sent to processing 1106. The signal is then processed, analyzed and mapped to an Audio/Video/Haptic Output 1108 and displayed on the augmented reality glasses 1112.

In an embodiment, strap 1110 is a head strap for securing the AR+BCI to the human head. In some embodiments, such as an implantable BCI, and AR system, the strap may not be necessary. The strapless system may use smart glasses or contact lenses. There may be multiple sensors, but no less than one sensor, in different embodiments. After seeing the output, the user may have different bio-signals from the brain, and as such this is a closed-loop biofeedback system. As the user focuses more on the SSVEP stimuli, the audio may feedback by frequency, power (volume), and selected cue audio to assist the human in reinforcing their focus on the stimuli. This may also occur with the vibration type and intensity of the haptics, as well additional peripheral visual cues in the display. These feedbacks are independent to the audio and haptics that may play back through the AR headset via a smartphone. It is even possible to remotely add to the sensory mix that of olfactory (smell) feedback that actually travels through entirely different parts of the brain that has been shown to be one of the strongest bio-feedback reinforcements in human cognitive training.

As a non-limiting example, when someone uses the BCI for the first time, they are considered a "Naïve" user, or one who's brain has never been trained with this kind of user interface. As a user continues to use it, their brain becomes less naïve and more capable and trained. They may become quicker and quicker at doing it. This is reinforcement learning—the BCI enables someone to align their intention and attention to an object and click it.

In an embodiment, to enrich the user interface experience, multiple feedback modalities (auditory, visual, haptic, and olfactory) may be available for choosing the most advantageous feedback modality for the individual or for the type of training. For example, when an appropriate brain wave frequency is generated by the user, real-time feedback about the strength of this signal may be represented by adjusting the intensity and frequency of the audio or haptic feedback. In addition, the possibility of using multimodal feedback means that multiple sensory brain regions are stimulated simultaneously, which enhances the neural signal and representation of feedback, thereby accelerating learning and neural plasticity.

An advantage of using odors as reinforcers may be due to the direct link between the brain areas that sense smell (olfactory cortex) and those that form memories (hippocampus) and produce emotions (amygdala). Odors may strengthen memory encoding, consolidation, and trigger recall.

Figure 12:
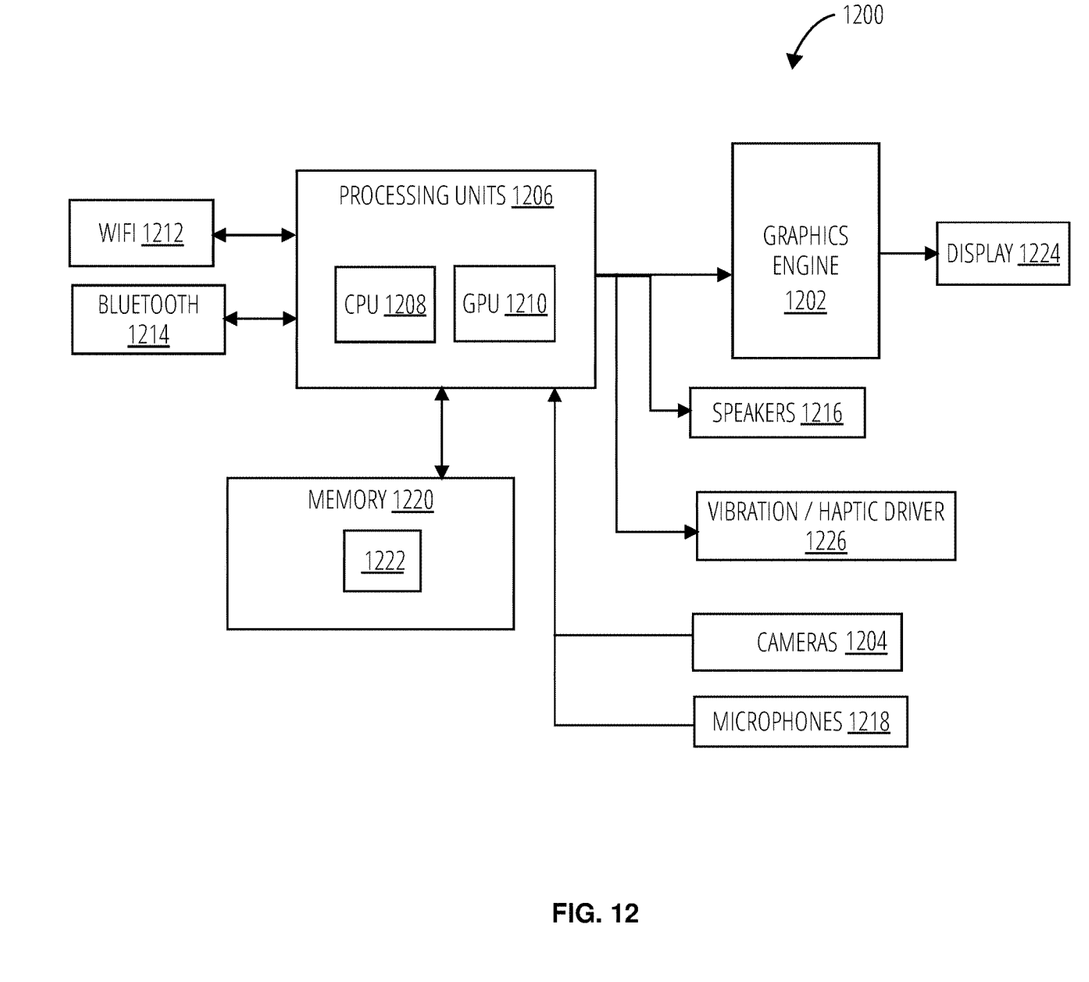
FIG. 12 illustrates an augmented reality device logic 1200 in accordance with one embodiment.

FIG. 12 illustrates components of an exemplary augmented reality device logic 1200. The augmented reality device logic 1200 comprises a graphics engine 1202, a camera 1204, processing units 1206, including one or more CPU 1208 and/or GPU 1210, a WiFi 1212 wireless interface, a Bluetooth 1214 wireless interface, speakers 1216, microphones 1218, one or more memory 1220, logic 1222, a visual display 1224, and vibration/haptic driver 1226.

The processing units 1206 may in some cases comprise programmable devices such as bespoke processing units optimized for a particular function, such as AR related functions. The augmented reality device logic 1200 may comprise other components that are not shown, such as dedicated depth sensors, additional interfaces, etc.

Some or all of the components in FIG. 12 may be housed in an AR headset. In some embodiments, some of these components may be housed in a separate housing connected or in wireless communication with the components of the AR headset. For example, a separate housing for some components may be designed to be worn or a belt or to fit in the wearer's pocket, or one or more of the components may be housed in a separate computer device (smartphone, tablet, laptop or desktop computer etc.) which communicates wirelessly with the display and camera apparatus in the AR headset, whereby the headset and separate device constitute the full augmented reality device logic 1200.

The memory 1220 comprises logic 1222 to be applied to the processing units 1206 to execute. In some cases, different parts of the logic 1222 may be executed by different components of the processing units 1206. The logic 1222 typically comprises code of an operating system, as well as code of one or more applications configured to run on the operating system to carry out aspects of the processes disclosed herein.

The apparatuses, methods, and systems in this disclosure are described in the preceding on the basis of several preferred embodiments. Different aspects of different variants are considered to be described in combination with each other such that all combinations that upon reading by a skilled person in the field on the basis of this document may be regarded as being read within the concept of the invention. The preferred embodiments do not limit the extent of protection of this document.

Having thus described embodiments of the present invention of the present application in detail and by reference to illustrative embodiments thereof, it will be apparent that modifications and variations are possible without departing from the scope of the present invention.

What is claimed is:

1. A method of implementing a brain computer interface (BCI) in a wireless headset, comprising:
   utilizing an augmented reality display;
   generating at least one of visual, auditory, or haptic stimulation to a user's occipital lobe and a user's somatosensory cortex, the method producing detectable brain wave frequencies;
   processing the detectable brain wave frequencies, thereby facilitating mapping of bio-signals to digital commands;
   associating the digital commands to a device;
   operating the device according to the digital commands;
   stimulating the user's somatosensory cortex, wherein the stimulating includes biofeedback confirmation of the operating of the device;
   utilizing one or more sensors for reading a bio-signal from the user;
   utilizing a processing module, including a processor that analyzes and maps the bio-signal into an output on the augmented reality display, wherein the processing module has different user selectable modes that include a raw mode, a simmer mode, a cooked mode, and a human interface device-keyboard mode;
   utilizing at least one biofeedback device in communication with the processing module, wherein the at least one biofeedback device provides feedback to the user; and
   utilizing a battery, wherein the battery provides power to at least one of the augmented reality display, the one or more sensors, the processing module, the at least one biofeedback device, and combinations thereof.

2. The method of claim 1, wherein the bio-signal comprises at least one of EEG (Electroencephalography), ECG (Electrocardiography), EMG (Electromyography), EOG (Electrooculography), functional near-infrared spectroscopy (fNIRS), visually evoked potentials, audio evoked potentials, haptic evoked potentials, and motion evoked potentials.

3. The method of claim 1, wherein the processing performed by the processing module includes visually evoked potentials.

4. The method of claim 1, wherein the headset further comprises a printed circuit board, wherein the printed circuit board includes at least one of the one or more sensors, the processing module, the at least one biofeedback device, the battery, and combinations thereof.

5. The method of claim 4, wherein the printed circuit board can connect wirelessly to a mobile device or a computer, wherein the printed circuit board is configured to emulate a Bluetooth keyboard and output data to at least one of the mobile device, the computer, and the augmented reality display, the output data including at least one of: a letter; a character; a number, and combinations thereof.

6. The method of claim 1, wherein the bio-signal is processed and analyzed in real time.

7. The method of claim 1, wherein the raw mode streams a full EEG sensor stream of data for further processing locally or in a cloud via a mobile or desktop internet connected device, wherein the internet connected device is configured to perform at least one of filtering, recognizing, and interacting with the data.

8. The method of claim 1, wherein the cooked mode produces a fully processed custom message generated by a local recognizer and diagnoses, and no raw data is passed to the user.

9. The method of claim 1, wherein the simmer mode is a hybrid combination between the raw mode and the cooked mode, and the processing module intersperses a raw data stream with cooked messages.

10. The method of claim 1, wherein the different modes include a strapless mode, wherein the BCI uses smart glasses or smart contact lenses, an implantable brain computer interface, and an AR system.

11. A method of implementing a brain computer interface (BCI) in a wireless headset, the method comprising:
   utilizing an augmented reality display;
   generating at least one of visual, auditory, or haptic stimulation to a user's occipital lobe and a user's somatosensory cortex, the method producing detectable brain wave frequencies;
   processing the detectable brain wave frequencies, thereby facilitating mapping of bio-signals to digital commands;
   associating the digital commands to a device;
   operating the device according to the digital commands;
   stimulating the user's somatosensory cortex, wherein the stimulating includes biofeedback confirmation of the operating of the device;
   utilizing one or more sensors for reading a bio-signal from the user;
   utilizing a processing module, including a processor that analyzes and maps the bio-signal into an output on the augmented reality display, wherein the processing module has different modes that include at least one of a raw mode, a simmer mode, a cooked mode, a human interface device-keyboard mode, and combinations thereof;
   utilizing at least one biofeedback device in communication with the processing module, wherein the at least one biofeedback device stimulates a user's central and or peripheral nervous system;

utilizing a battery, wherein the battery provides power to at least one of the augmented reality display, the one or more sensors, the processing module, the at least one biofeedback device, and combinations thereof; and utilizing a printed circuit board includes at least one of the one or more sensors, the processing module, the at least one biofeedback device, the battery, and combinations thereof, wherein the printed circuit board is configured to emulate a Bluetooth keyboard and output data to at least one of a mobile device, a computer, and the augmented reality display, the output data including at least one of: a letter; a character; a number, and combinations thereof;

wherein the BCI utilizes AI machine learning for pattern recognition and personalization that operates while the BCI is not connected to a network, the AI machine learning acting as one or more of an auto-tuning dynamic noise reducer, a feature extractor, and a recognizer-categorizer;

wherein AI machine learning training is applied when the BCI is connected to the network to create an individualized recognizer-categorizer, derived outputs of the AI machine learning training being stored in an expert system knowledge base in cloud storage;

wherein synthesized insights derived from the AI machine learning and the expert system knowledge base in cloud storage are used to generate a downloadable individualized executable recognizer-categorizer downloadable via a wireless connection or wired connection between the network and a BCI storage device for offline usage;

wherein the method applies to resource constrained devices including wearable devices, implantable devices, and internet of things (IoT) devices; and wherein the different modes include a strapless mode, wherein the fully self-contained BCI uses smart glasses or smart contact lenses, an implantable brain computer interface, and an AR system.

* * * * *